United States Patent [19]

Shoesmith et al.

[11] Patent Number: Plant 5,491

[45] Date of Patent: Jun. 11, 1985

[54] CHRYSANTHEMUM PLANT NAMED FROSTY

[75] Inventors: Leonard H. Shoesmith, Surrey, United Kingdom; Peter S. Hesse, Bradenton, Fla.

[73] Assignee: Pan American Plant Company, Parrish, Fla.

[21] Appl. No.: 488,771

[22] Filed: Apr. 26, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of chrysanthemum plant named Frosty having flat capitulum form, single anemone flower type, white ray floret color, immature lime green to mature pale yellow disc florets, 35–45 mm. diameter across capitulum face, semi-upright branching habit, and its relatively short plant height.

2 Drawing Figures

The present invention comprises a new and distinct cultivar of *Chrysanthemum morifolium,* Ramat., hereinafter referred to by the cultivar name Frosty.

Frosty is a product of a planned breeding program which had the objective of creating new chrysanthemum cultivars with single anemone capitulum type, flat capitulum form, white ray florets and pale yellow disc florets, 9 week flowering response, and year round commercially acceptable quality for pot mum programs. Such traits in combination were not present in previously available commercial cultivars.

Frosty was originated from a hybridization made in a controlled breeding program in Westfield, Woking England in 1977. The male and female parents are unknown at this time. Frosty was discovered and selected as one flowering plant within the progeny of the stated parentage by Leonard H. Shoesmith and Peter S. Hesse in November, 1978 in a cotrolled environment in West Chicago, Ill., and given the code name P8-906-WS.

The first act of asexual reproduction of Frosty was accomplished when vegetative cuttings were taken from the initial selection in February, 1979 in a controlled environment in West Chicago, Ill. by a technician working under formulations established and supervised by Leonard H. Shoesmith and Peter S. Hesse. Horticultural examination of selected units initiated March, 1979 has demonstrated that the combination of characteristics as herein disclosed for Frosty are firmly fixed and are retained through successive generations of asexual reproduction.

Frosty has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Frosty, which in combination distinguish this chrysanthemum as a new and distinct cultivar:

1. Flat capitulum form.
2. Single anemone flower type.
3. The anemone disc florets are more developed and pronounced under low temperature conditions. Under high temperatures they are smaller and less pronounced.

4. White ray floret color.
5. Pale yellow (mature) to lime green (immature) disc florets.
6. Diameter across face of the capitulum 35–45 mm.
7. Relatively short pot plant height of about 225 mm. from edge of pot.
8. Semi-upright branching habit.

Of the many commercial cultivars known to the present inventors, the most similar in comparison to Frosty is Illini Windmill. Reference is made to attached Chart A, which compares certain characteristics of Frosty to those same characteristics of Illini Windmill. The principal distinguishing characteristic is the much smaller capitulum diameter of Frosty.

The accompanying photographic drawings show typical inflorescence and foliage characteristics of Frosty, with colors being as nearly true as possible with illustrations of this type. Sheet 1 is a color photograph of Frosty. Sheet 2 is a black and white print of a photograph showing an abaxial view of Frosty at various stages of growth.

In the following description color references are made to The Royal Horticultural Society Colour Chart. The color values were determined between 8:00–9:00 A.M. on Nov. 17, 1982 under 2000–3000 foot candle light intensity at Parrish, Fla.

Classification:

*Botanical.*—*Chrysanthemum morifolium,* Ramat.,cv FROSTY.

*Commercial.*—Anemone pot mum.

INFLORESCENCE

A. Capitulum:

*Form.*—Flat.

*Type.*—Anemone.

*Diameter across face.*—35–45 mm.

B. Corolla of ray florets:

*Color (general tonality from a distance of three meters).*—White.

*Color (abaxial).*—155D.

*Color (adaxial).*—155D.

C. Corolla of disc florets:

*Color (mature).*—4B.

*Color (immature).*—154A.

D. Reproductive organs:

*Androecium.*—Present in disc florets only; numerous.

*Gynoecium.*—Present in both ray and disc florets; numerous.

PLANT

A. General appearance:

*Height.*—From edge of pot, about 225 mm.

B. Foliage:

*Color (abaxial).*—147B.

*Color (adaxial).*—147A.

*Shape.*—Deeply lobed and serrate, elliptical.

CHART A

| | FROSTY | ILLINI WINDMILL |
|---|---|---|
| Diameter across face of capitulum | 35–45 mm. | 60–70 mm. |
| Ray floret color | white | white |
| Disc floret color | Pale yellow | Bright yellow |
| Capitulum type | Anemone | Anemone |
| Plant height | 200–250 mm. | 180–230 mm. |
| Flower response | 9 weeks | 9 weeks |
| Leaf shape | Elliptical and serrate | Ovate and less serrate |

We claim:

1. A new and distinct cultivar of chrysanthemum plant named Frosty, as described and illustrated, and particularly characterized by its flat capitulum form, single anemone flower type, white ray floret color, immature lime green to mature pale yellow disc florets, 35–45 mm. diameter across capitulum face, semi-upright branching habit, and its relatively short plant height.

* * * * *

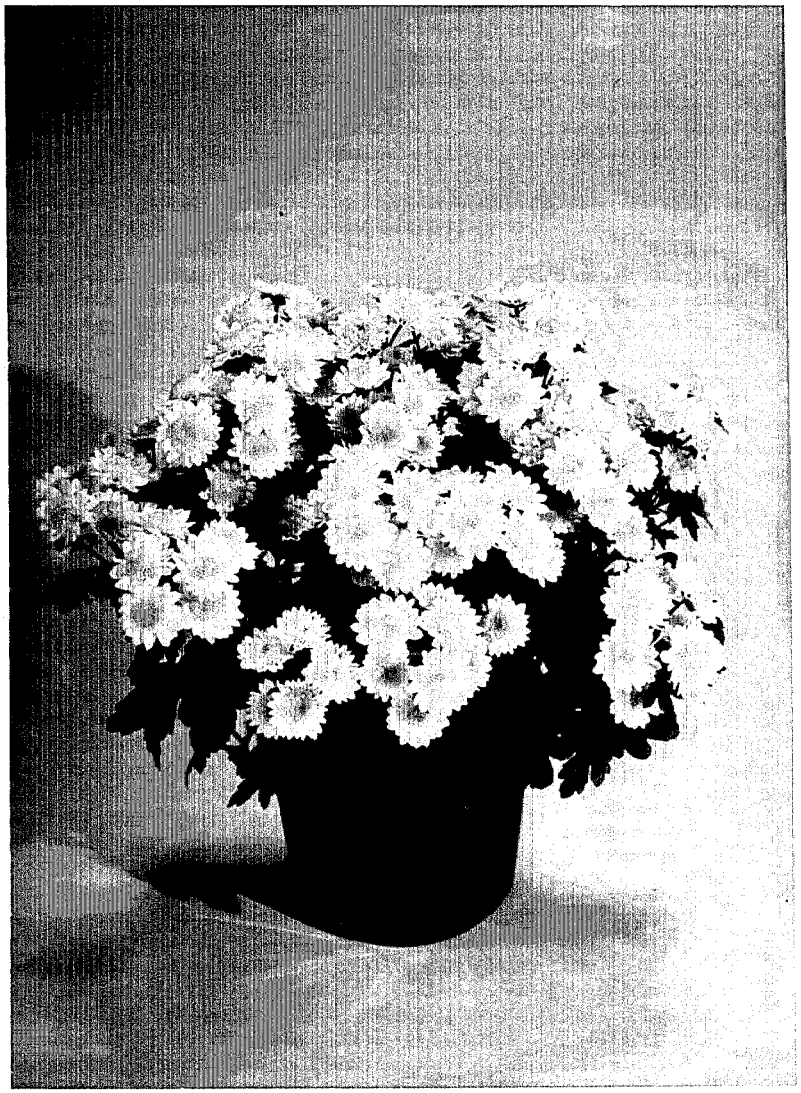

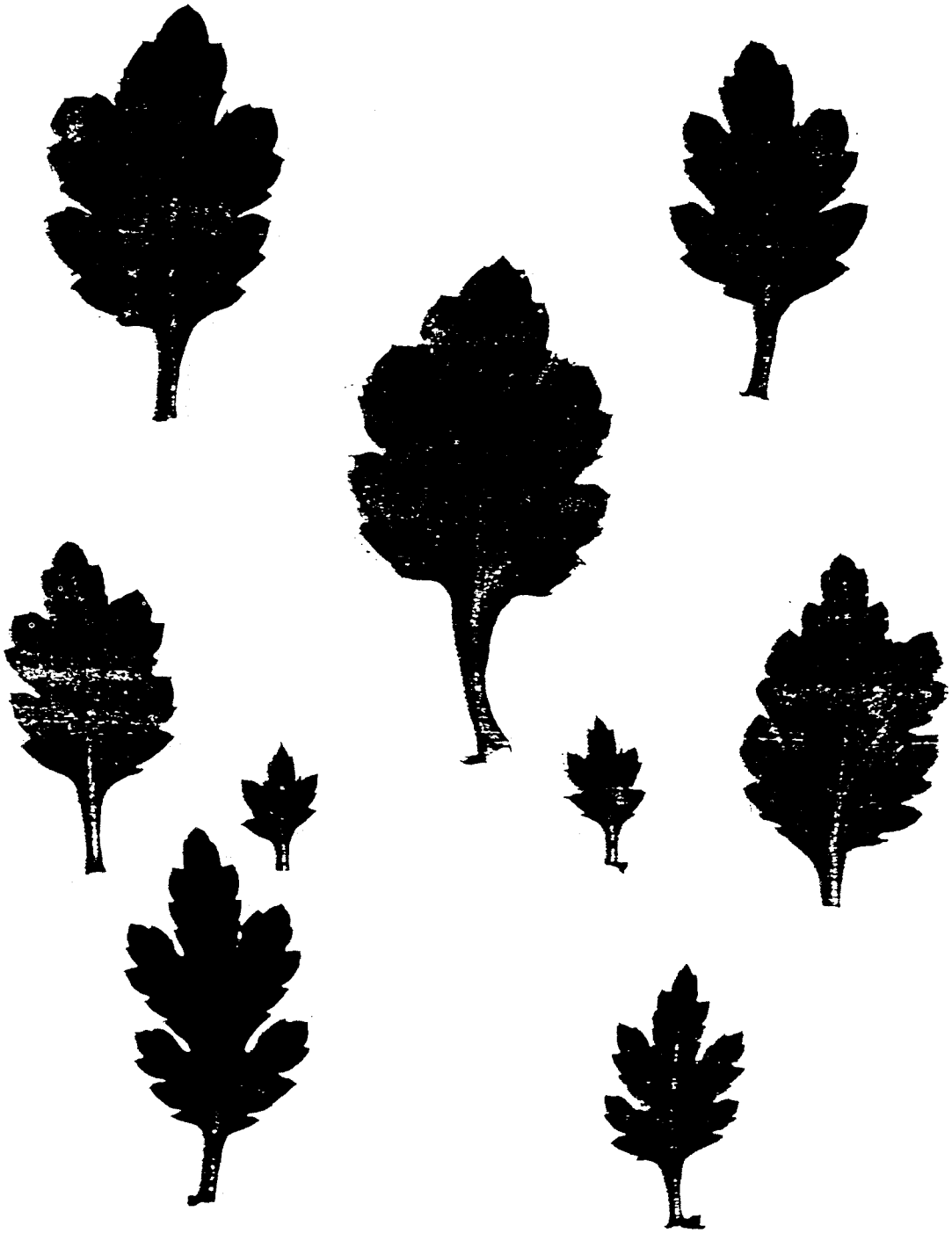
FROSTY
(abaxial)